(12) United States Patent
Kwon et al.

(10) Patent No.: US 7,799,878 B2
(45) Date of Patent: Sep. 21, 2010

(54) DINUCLEAR TRANSITION METAL COMPOUND, CATALYST COMPOSITION COMPRISING THE SAME, METHOD OF PREPARING OLEFIN POLYMER, AND OLEFIN POLYMER PRODUCED USING THE METHOD

(75) Inventors: Heon Yong Kwon, Daejeon (KR); Ki-soo Lee, Daejeon (KR); Yonggyu Han, Daejeon (KR); Byoungho Jeon, Daejeon (KR); You Young Jung, Daejeon (KR); Baekun Shin, Incheon (KR)

(73) Assignee: LG Chem, Ltd. (KR)

( * ) Notice: Subject to any disclaimer, the term of this patent is extended or adjusted under 35 U.S.C. 154(b) by 828 days.

(21) Appl. No.: 11/563,946

(22) Filed: Nov. 28, 2006

(65) Prior Publication Data
US 2007/0203018 A1    Aug. 30, 2007

(30) Foreign Application Priority Data
Nov. 28, 2005    (KR) .................. 10-2005-0114045

(51) Int. Cl.
*C08F 4/52* (2006.01)
(52) U.S. Cl. .................. 526/114; 526/135; 502/103
(58) Field of Classification Search ................ 526/114, 526/135; 502/103
See application file for complete search history.

(56) References Cited

U.S. PATENT DOCUMENTS 6,576,779 B1    6/2003    Bansleben et al.

FOREIGN PATENT DOCUMENTS

EP    0 874 005    10/1998

OTHER PUBLICATIONS

S, Sujith, et al.; "Ethylene/Polar Norbornene Copolymerizations by Bimetallic Salicylaldimine-Nickel Catalysts"; Macromolecules; vol. 38; pp. 10027-10033; 2005.
Karvembu, et al.; " Binuclear ruthenium (III) complexes: synthesis, characterisation, catalytic activity in aryl-aryl couplings and biological activity"; Transition Metal Chemistry; vol. 27; pp. 631-638; 2002.
Chen, et al.; "Synthesis of Functional Olefin Copolymers with Controllabel Topolgies Using a Chain-Walking Catalyst"; J. Am. Chem. Soc.; vol. 125; pp. 6697-6704; 2003.
Sun, et al.; "Vinyl Polymerization of Norbornene with Neutral Salicylaldiminato Nickel (II) Complexes"; Organometallics; vol. 22; pp. 3678-3683; 2003.
International Search Report dated Feb. 22, 2007 for Application No. PCT/KR2006-005019 (All references cited in Search Report are listed above).

*Primary Examiner*—Ling-Siu Choi
*Assistant Examiner*—Sonya Wright
(74) *Attorney, Agent, or Firm*—Cantor Colburn LLP

(57) ABSTRACT

A dinuclear transition metal compound of Formula 1 is provided:

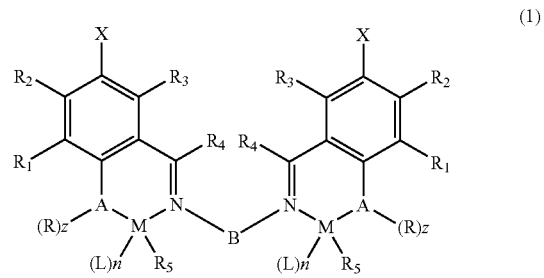

(1)

where $R_1$, $R_2$, $R_3$, $R_4$, $R_5$, R, L, A, B, X, M, z, and n are the same as in the description of the present invention. The dinuclear transition metal compound includes two transition metal compounds connected each other by a bridging group so that a decrease in catalyst activation due to a polar functional group can be prevented. A catalyst composition including the dinuclear transition metal compound is highly active for a monomer having a polar functional group.

28 Claims, No Drawings

DINUCLEAR TRANSITION METAL COMPOUND, CATALYST COMPOSITION COMPRISING THE SAME, METHOD OF PREPARING OLEFIN POLYMER, AND OLEFIN POLYMER PRODUCED USING THE METHOD

CROSS-REFERENCE TO RELATED PATENT APPLICATIONS

This application claims the benefit of Korean Patent Application No. 10-2005-0114045, filed on Nov. 28, 2005, in the Korean Intellectual Property Office, the disclosure of which is incorporated herein in its entirety by reference.

BACKGROUND OF THE INVENTION

1. Field of the Invention

The present invention relates to a novel dinuclear transition metal compound, a catalyst composition including the same, a method of preparing an olefin polymer, and an olefin polymer produced using the method, and more particularly, to a novel dinuclear transition metal compound which includes two complexes bridged each other in which transition metals including nickel are coordinated to a novel tetradentate ligand having salicylaldimine derivatives, a catalyst composition including the novel dinuclear transition metal compound and a cocatalyst, a method of preparing an olefin polymer, and an olefin polymer produced using the method.

2. Description of the Related Art

In general, a transition metal compound to which a salicylaldimine ligand is introduced is a transition metal compound where a Group 4 transition metal, such as titanium, zirconium, or hafnium, a transition metal, such as copper or zinc, or a Group 10 transition metal, such as nickel or palladium is coordinated with one or two salicylaldimine groups. Such transition metal compounds can be used for olefin polymerization, in particular, copolymerization of ethylene with a comonomer having a polar functional group.

For example, Fujita, T. of Mitsui Chemicals in 1999 found that in a case of a Group 4 transition metal, such as titanium, zirconium, or hafnium, by introducing a salicylaldimine ligand having various substituents to an amine, the obtained catalyst system was very active for polymerization of olefin, such as ethylene or propylene, which is disclosed in EP No. 0874005.

Meanwhile, it is known that a late transition metal, such as nickel or palladium, is highly active for polymerization of olefin and has low affinity with respect to functional groups so that it provides high activity in polymerization of polar monomers having a functional group.

For example, U.S. Pat. No. 6,576,779 B1 discloses that a nickel or palladium compound to which a salicylaldimine ligand is introduced is highly active for homopolymerization of olefin and copolymerization of olefin with a polar monomer.

However, since a conventional transition metal compound including a salicylaldimine ligand includes only one transition metal acting as active site per molecule, it was difficult to effectively prevent a decrease in catalyst activation due to a polar functional group.

Accordingly, there is a need to develop a novel transition metal compound including a salicylaldimine ligand which prevents a decrease in catalyst activation due to a polar functional group by overcoming the structural limitation of a conventional transition metal compound.

SUMMARY OF THE INVENTION

The present invention provides a novel dinuclear transition metal compound including salicylaldimine ligands connected by a bridging group.

The present invention also provides a catalyst composition including the dinuclear transition metal compound.

The present invention also provides a method of preparing an olefin polymer using the catalyst composition.

The present invention also provides an olefin polymer produced using the method.

According to an aspect of the present invention, there is provided a dinuclear transition metal compound represented by Formula 1:

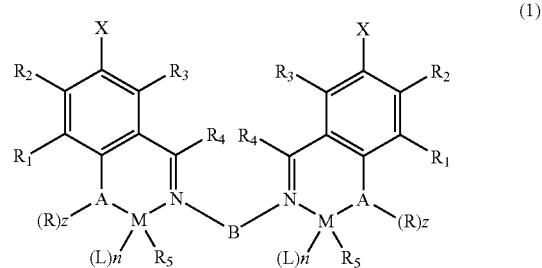

(1)

where R is each independently a hydrogen atom, C1-C11 alkyl, or substituted or unsubstituted aryl, wherein when A is oxygen or sulfur, z is 0, and when A is nitrogen, z is 1;

$R_1$ is each independently a hydrogen atom, C1-C11 alkyl, substituted or unsubstituted arylalkyl or substituted or unsubstituted aryl;

$R_2$ is each independently a hydrogen atom, substituted or unsubstituted aryl, C1-C11 alkyl, or a halogen atom, or can be a substituted or unsubstituted hydrocarbyl which can form an aromatic or nonaromatic carbocyclic ring together with $R_1$;

$R_3$ is a hydrogen atom;

$R_4$ is each independently a hydrogen atom, C1-C11 alkyl, or a substituted or unsubstituted aryl, or can be a substituted or unsubstituted hydrocarbyl which can form a nonaromatic carbocyclic ring together with $R_3$;

n is 0 or 1;

when n is 1, $R_5$ is unsubstituted or substituted aryl, C1-C11 alkyl, a hydrogen atom, or a halogen atom, and when n is 0, $R_5$ is substituted or unsubstituted allyl, or a derivative to which halogen, nitro, or sulfonate group is introduced;

L is each independently a coordination ligand selected from triphenylphosphine, tri(C1-C6 alkyl)phosphine, tricycloalkyl phosphine, diphenyl alkyl phosphine, dialkylphenylphosphine, triphenoxyphosphine, trialkylamine, C2-20 alkene, halogen, ester, substituted C2-C4 alkene, C1-C4 alkoxy, pyridine, di(C1-C3 alkyl)ether, tetrahydrofurane, and nitrile;

X is each independently an electron acceptor group selected from a hydrogen atom, $NO_2$, halogen, sulfonate ($SO_3^-$), sulfonyl ester ($SO_2R$), carboxyl($COO^-$), perfluoroalkyl, and carboxylic ester;

M is each independently a Group VI, VII or VII transition metal selected from Fe, Co, Ni, Ru, Rh, Pd, Os, Ir, and Pt;

A is each independently oxygen, nitrogen, or sulfur; and

B is a covalent bridging group connecting two nitrogen atoms and is carbylene group, a silane group, a disilane group, substituted or unsubstituted C1-C60 hydrocarbylene group, or a substituted or unsubstituted C1-C60 heterohydrocarbylene group including Group 4B, 5B, or 6B atom, wherein a substituent of the substituted arylalkyl, aryl, allyl, alkene, hydrocarbylene, or heterohydrocarbylene is each independently a C1-C4 alkyl group, a perfluoroalkyl group, a nitro group, a sulfonate group, a halogen group, an arylalkyl group, a siloxyl group (—$OSiE_3$) where E is phenyl or C1-C4 alkyl, or a hydrocarbyl-terminated oxyhydrocarbylene group (-(GO)z$R_7$) where G is each independently a C1-C4 alkylene group or arylene group, O is oxygen, $R_7$ is a C1-C11 hydrocarbyl group, and z is an integer from 1 to 4.

The dinuclear transition metal compound can also be represented by Formula 2:

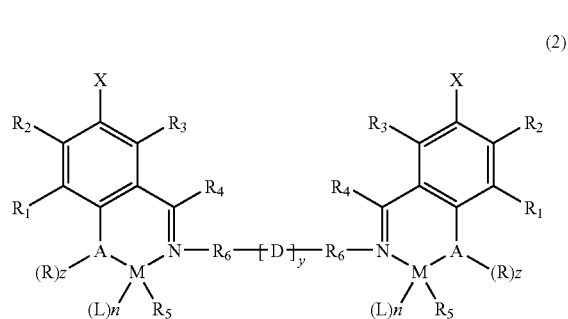

(2)

where $R_6$ is each independently substituted or unsubstituted C1-C12 alkylene, cycloalkylene, arylene, alkylarylene, arylalkylene, or oxyhydrocarbylene (-(GO)$_m$G-) where G is C1-C4 alkylene or arylene and m is an integer from 1 to 4;

D is saturated or unsaturated alkylene, sulfone, azo, or a carbonyl group, wherein the saturated alkylene includes —(CR$_a$R$_b$)$_y$— where $R_a$ and $R_b$ are each independently a hydrogen atom, C1-C20 alkyl, or C1-C20 aryl, the unsaturated alkylene includes —(CH=CH)$_y$—, and y is an integer from 0 to 50; and $R_1$, $R_2$, $R_3$, $R_4$, $R_5$, L, R, M, A, X, z, and n are the same as described above.

The dinuclear transition metal compound can also be represented by Formula 3:

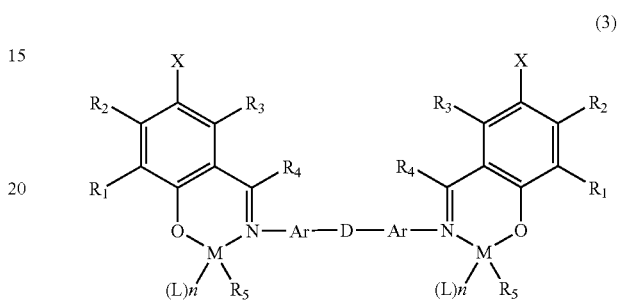

(3)

where Ar is a substituted or unsubstituted arylene group; and $R_1$, $R_2$, $R_3$, $R_4$, $R_5$, L, M, D and n are the same as described above.

The dinuclear transition metal compound can also be represented by Formula 4:

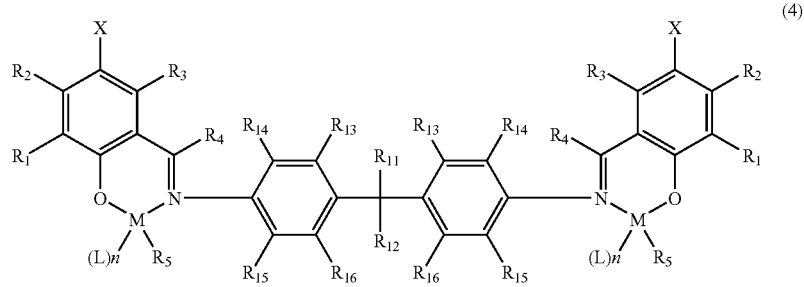

(4)

where $R_{11}$, $R_{12}$, $R_{13}$, $R_{14}$, $R_{15}$, and $R_{16}$ are each independently a hydrogen atom, a halogen atom, C1-C8 alkyl, or C1-C8 aryl; and $R_1$, $R_2$, $R_3$, $R_4$, $R_5$, L, M, and n are the same as described above.

The dinuclear transition metal compound can also be represented by Formula 5:

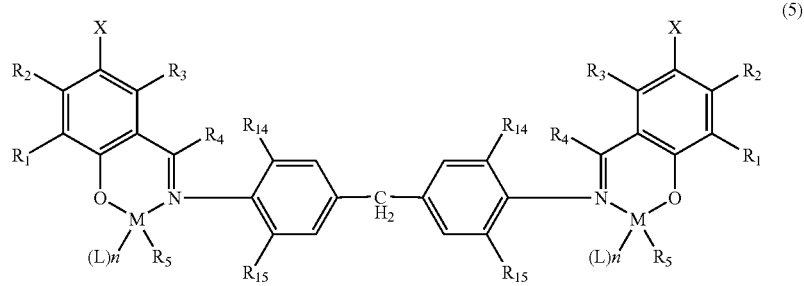

(5)

where $R_{14}$ and $R_{15}$ are each independently C1-C4 alkyl;

M is nickel; and $R_1$, $R_2$, $R_3$, $R_4$, $R_5$, L, and n are the same as described above.

According to another embodiment of the present invention, there is provided a catalyst composition including the dinuclear transition metal compound and at least one cocatalyst selected from alkylaluminoxane, alkylaluminium, and Lewis acid.

In the catalyst composition, the alkylaluminoxane may be represented by Formula 6:

$$*-\!\!\left[\!\!\begin{array}{c}R^{20}\\|\\Al-O\end{array}\!\!\right]_{\!\!n}\!\!-\!* \qquad (6)$$

where $R^{20}$ is a hydrogen atom, a unsubstituted or substituted C1-C20 alkyl group, a unsubstituted or substituted C3-C20 cycloalkyl group, a C6-C40 aryl group, a C6-C40 alkylaryl group, or a C6-C40 arylalkyl group; and n is an integer from 1 to 100.

In the catalyst composition, the alkylaluminium may be represented by Formula 7:

$$R^{22}\!\!\diagdown\!\!\overset{\overset{\displaystyle R^{21}}{|}}{Al}\!\!\diagup\!\!R^{23} \qquad (7)$$

where $R^{21}$, $R^{22}$, and $R^{23}$ are each independently or at the same time a hydrogen atom, a halogen atom, a unsubstituted or substituted C1-C20 alkyl group, a unsubstituted or substituted C3-C20 cycloalkyl group, a C6-40 aryl group, a C6-40 alkylaryl group, or a C6-40 arylalkyl group, and at least one of $R^{21}$, $R^{22}$, and $R^{23}$ comprises an insubstituted or substituted $C_1$-$C_{20}$ alkyl group.

In the catalyst composition, the Lewis acid may be represented by Formula 8:

$$M(R^{24})_q \qquad (8)$$

where M is a Groups 3 through 11 transition metal shown in Periodic Table of Elements;

$R^{24}$ is each independently C1-C20 hydrocarbyl; and q is an integer of 2 through 4.

According to another embodiment of the present invention, there is provided a method of preparing an olefin-based polymer, the method including contacting a monomer with the catalyst composition.

In the method, the monomer may include at least one monomer selected from the group consisting of ethylene, a carbonic acid represented by Formula 10, a carbonic acid ester represented by Formula 11 or Formula 12, alkyl vinyl ether represented by Formula 13, vinyl ketone represented by Formula 14, and vinyl alcohol represented by Formula 15:

$$CH_2\!=\!CH(CH_2)_m COOH \qquad (10),$$

$$CH_2\!=\!CH(CH_2)_m CO_2 R^{25} \qquad (11)$$

$$CH_2\!=\!CH(CH_2)_m OCOR^{25} \qquad (12),$$

$$CH_2\!=\!CH(CH_2)_m OR^{25} \qquad (13)$$

$$CH_2\!=\!CH(CH_2)_m C(O)R^{25} \qquad (14), \text{ and}$$

$$CH_2\!=\!CH(CH_2)_m OH \qquad (15)$$

where m is an integer from 0 to 10; and $R^{25}$ is C1-C10 hydrocarbyl.

The olefin polymerization may be carried out through slurry polymerization, liquid polymerization, vapor polymerization, or mass polymerization.

The olefin polymerization may be carried out at a pressure of 0.01-1000 atm.

In the method of preparing an olefin-based polymer, when the monomer is a monomer mixture of ethylene and a comonomer including a polar functional group, the amount of ethylene may be in the range of 60-99 mol % and the amount of the comonomer may be in the range of 1-40 mol %, based on the total amount of the monomer mixture.

According to another embodiment of the present invention, there is provided an olefin-based polymer prepared using the method.

The olefin-based polymer may be a polar copolymer including 60-99 mol % of ethylene and 1-40 mol % of a polar comonomer.

DETAILED DESCRIPTION OF THE INVENTION

The present invention will now be described more fully with reference to the accompanying drawings.

Unlike a conventional transition metal compound including a salicylaldimine ligand, a transition metal compound according to an embodiment of the present invention consists of two transition metal compounds connected each other by a bridging group so that a decrease in catalyst activation due to a polar functional group can be prevented. A catalyst composition including the transition metal compound is highly active for a monomer having a polar functional group.

A dinuclear transition metal compound can be represented by Formula 1:

where R is each independently a hydrogen atom, C1-C11 alkyl, substituted or unsubstituted aryl, alkoxy, alkenyl, aryloxy, or heteroaryl wherein when A is oxygen or sulfur, z is 0, and when A is nitrogen, z is 1;

$R_1$ is each independently a hydrogen atom, C1-C12 alkyl, substituted or unsubstituted arylalkyl or substituted or unsubstituted aryl;

$R_2$ is each independently a hydrogen atom, substituted or unsubstituted aryl, C1-C11 alkyl, or a halogen atom, or can be a substituted or unsubstituted hydrocarbyl which can form an aromatic or nonaromatic carbocyclic ring together with $R_1$;

$R_3$ is a hydrogen atom;

$R_4$ is each independently a hydrogen atom, C1-C11 alkyl, or a substituted or unsubstituted aryl, or can be a substituted or unsubstituted hydrocarbyl which can form a nonaromatic carbocyclic ring together with $R_3$;

n is 0 or 1;

when n is 1, $R_5$ is unsubstituted or substituted aryl, C1-C11 alkyl, a hydrogen atom, or a halogen atom, and when n is 0, $R_5$ is substituted or unsubstituted allyl, or a derivative to which halogen, nitro, or sulfonate group is introduced;

L is each independently a coordination ligand selected from triphenylphosphine, tri(C1-C6 alkyl)phosphine, tricycloalkyl phosphine, diphenyl alkyl phosphine, dialkylphenylphosphine, triphenoxyphosphine, trialkylamine, C2-20 alkene, halogen, ester, substituted C2-C4 alkene, C1-C4 alkoxy, pyridine, di(C1-C3 alkyl)ether, tetrahydrofurane, and nitrile;

X is each independently an electron acceptor group selected from a hydrogen atom, $NO_2$, halogen, sulfonate ($SO_3^-$), sulfonyl ester ($SO_2R$), carboxyl($COO^-$), perfluoroalkyl, and carboxylic ester;

M is each independently transition metal selected from Group VI, VII or VIII transition metal, more preferably each independently a Group VI, VII or VIII transition metal selected from Fe, Co, Ni, Ru, Rh, Pd, Os, Ir, and Pt;

A is each independently oxygen, nitrogen, or sulfur; and

B is a covalent bridging group connecting two nitrogen atoms and is carbylene group, a silane group, a disilane group, substituted or unsubstituted C1-C60 hydrocarbylene group, or a substituted or unsubstituted C1-C60 heterohydrocarbylene group including Group 4B, 5B, or 6B atom, wherein a substituent of the substituted arylalkyl, aryl, allyl, alkene, hydrocarbylene, or heterohydrocarbylene is each independently a C1-C4 alkyl group, a perfluoroalkyl group, a nitro group, a sulfonate group, a halogen group, an arylalkyl group, a siloxyl group ($-OSiE_3$) where E is phenyl or C1-C4 alkyl, a hydrocarbyl-terminated oxyhydrocarbylene group (-(GO)z $R_7$) where G is each independently a C1-C4 alkylene group or arylene group, O is oxygen, $R_7$ is a C1-C11 hydrocarbyl group, and z is an integer from 1 to 4, an alkoxy group, alkenyl group, aryloxy group, or a heteroaryl group.

In Formula 1, when $R_1$ is alkyl, the alkyl may be a linear or branched C1-C6 alkyl, when $R_1$ is aryl, the aryl may be phenyl, biphenyl, naphthyl, anthracyl, or phenanthracyl, when $R_1$ is a substituted aryl, the substituted aryl may be an aryl substituted with fluoroalkyl, nitro, sulfonate, or halogen, when $R_1$ is arylalkyl, the arylalkyl may be tolyl; G may be C2-C3 alkylene or phenylene; and $R_7$ may be C1-C3 alkyl.

In particular, $R_1$ may have a substitutent having large steric hindrance and can be a branched C3-C6 alkyl or alkoxyalkyl, phenyl, anthracenyl, phenanthrenyl, terphenyl, or tert-butyl.

The binuclear transition metal compound includes two late transition metals per molecule so that a decrease in catalyst activation due to chemical substances including an oxygen atom can be prevented. In addition, the binuclear transition metal compound includes a salicylaldimine ligand that is a bidentate ligand so that selectivity in polymerization of ethylene with α-olefin can be more easily controlled.

The dinuclear transition metal compound can also be represented by Formula 2:

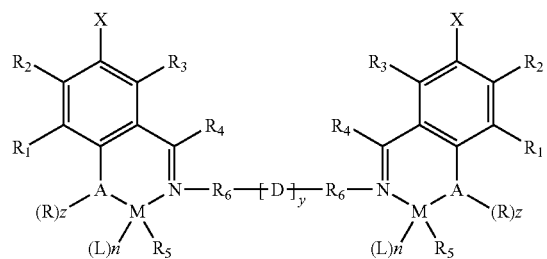

(2)

where $R_6$ is each independently substituted or unsubstituted C1-C12 alkylene, cycloalkylene, arylene, alkylarylene, arylalkylene, or oxyhydrocarbylene (-$(GO)_mG$-) where G is C1-C4 alkylene or arylene and m is an integer from 1 to 4, wherein the cycloalkylene may have 5-11 carbons, the arylene may have 5-11 carbons, the alkylarylene may have 6-11 carbons, and the arylalkylene may have 6-11 carbons;

D is saturated or unsaturated alkylene, sulfone, azo, or a carbonyl group, wherein the saturated alkylene includes —$(CR_aR_b)_y$— where $R_a$ and $R_b$ are each independently a hydrogen atom, C1-C20 alkyl, or C1-C20 aryl, the unsaturated alkylene includes —$(CH=CH)_y$—, and y is an integer from 0 to 50; and $R_1$, $R_2$, $R_3$, $R_4$, $R_5$, L, R, M, A, X, z, and n are the same as described above.

$R_6$ can be a cycloalkylene group, such as a C4-C8 alkyl group, a 4-cyclohexylene group, a phenylene group, a biphenylene group, a naphthylene group, or an arylene group which has C1-C4 hydrocarbon at an ortho site of a benzene ring thereof.

The dinuclear transition metal compound can also be represented by Formula 3:

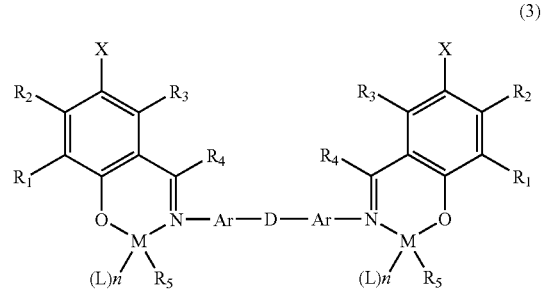

(3)

where Ar is a substituted or unsubstituted arylene group; and $R_1$, $R_2$, $R_3$, $R_4$, $R_5$, L, M, D and n are the same as described above.

The dinuclear transition metal compound can also be represented by Formula 4:

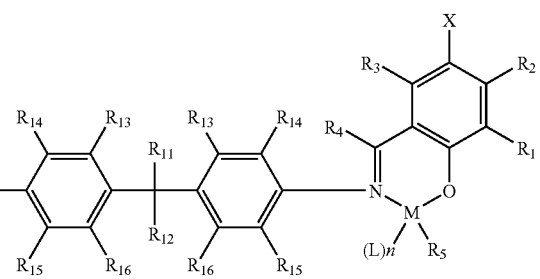

(4)

where $R_{11}, R_{12}, R_{13}, R_{14}, R_{15}$, and $R_{16}$ are each independently a hydrogen atom, a halogen atom, a C1-C8 alkyl group, or a C1-C8 aryl group; and $R_1, R_2, R_3, R_4, R_5$, L, M, and n are the same as described above.

The dinuclear transition metal compound can also be represented by Formula 5:

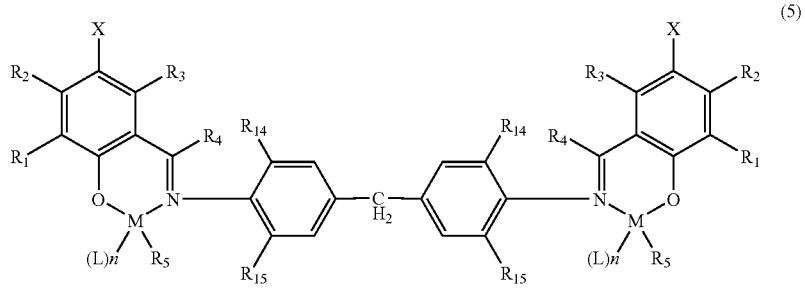

(5)

where $R_{14}$ and $R_{15}$ are each independently a C1-C4 alkyl group;

M is nickel;

$R_1, R_2, R_3, R_4, R_5$, L, and n are the same as described above.

A method of preparing the dinuclear transition metal compound according to an embodiment of the present invention will now be described in detail.

The method includes: reacting a ligand compound represented by Formula 1A with a reductant to obtain a metal salt compound represented by Formula 1B; and reacting the metal salt compound of Formula 1B with a transition metal compound represented by Formula 1C:

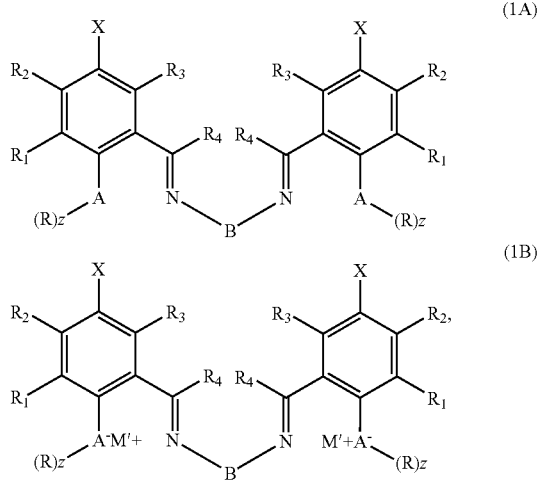

and

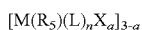  (1C)

where M is an alkali metal;

a is 1 or 2; and $R_1, R_2, R_3, R_4, R_5$, L, A, B, X, M, and n are the same as described above.

In the method of preparing the dinuclear transition metal compound, the reductant may be n-butyllithium, sec-butyllithium, tert-butyllithium, methyllithium, lithiumbistrimethylsilylamid, sodiumhydroxide, potassiumhydroxide, sodiummethoxide, sodium ethoxide, potassium tert-butoxide, methylmagnesiumchloride, ethylmagnesiumbromide, dimethylmagnesium, metal lithium, metal sodium, metal potassium, or the like, but is not limited thereto. That is, the reductant can be any reductant that is used in the art.

A catalyst composition used to polymerize olefin according to an embodiment of the present invention includes a dinuclear transition metal compound and at least one cocatalyst selected from alkylaluminoxane, alkylaluminium, and Lewis acid.

In the catalyst composition, the alkylaluminoxane may be represented by Formula 6:

(6)

where $R^{20}$ is a hydrogen atom, a unsubstituted or substituted C1-C20 alkyl group, a unsubstituted or substituted C3-C20 cycloalkyl group, a C6-C40 aryl group, a C6-C40 alkylaryl group, or a C6-C40 arylalkyl group; and n is an integer from 1 to 100.

In the catalyst composition, the alkylaluminium may be represented by Formula 7:

(7)

where $R^{21}, R^{22}$, and $R^{23}$ are each independently or at the same time a hydrogen atom, a halogen atom, a unsubstituted or substituted C1-C20 alkyl group, a unsubstituted or substituted C3-C20 cycloalkyl group, a C6-40 aryl group, a C6-40 alkylaryl group, or a C6-40 arylalkyl group, and at least one of $R^{21}, R^{22}$, and $R^{23}$ comprises an unsubstituted or substituted $C_1$-$C_{20}$ alkyl group.

In the catalyst composition, the Lewis acid may be represented by Formula 8:

$M(R^{24})_q$  (8)

where M is a Groups 3 through 11 transition metal shown in Periodic Table of Elements;

R²⁴ is each independently C1-C20 hydrocarbyl; and
q is an integer of 2 through 4.

M can be a Group 10 transition metal, and particularly, nickel. R²⁴ can be cycloalkyl, and particularly cyclooctadiene.

A method of preparing an olefin-based polymer according to an embodiment of the present invention includes contacting a monomer with the catalyst composition.

In the method, the monomer includes at least one monomer selected from the group consisting of ethylene, a carbonic acid represented by Formula 10, a carbonic acid ester represented by Formula 11 or Formula 12, alkyl vinyl ether represented by Formula 13, vinyl ketone represented by Formula 14, and vinyl alcohol represented by Formula 15:

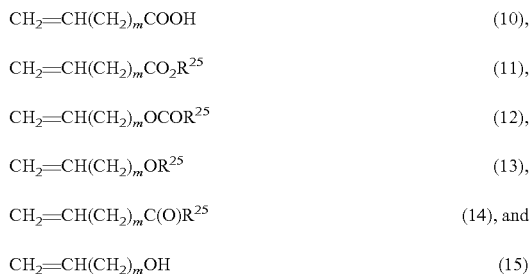

where m is an integer from 0 to 10; and
R²⁵ is C1-C10 hydrocarbyl.

By using the method of preparing an olefin-based polymer according to an embodiment of the present invention, homo polymerization of only a nonpolar monomer and copolymerization of a nonpolar monomer and a polar monomer can be carried out.

The olefin polymerization may be carried out through slurry polymerization, liquid polymerization, vapor polymerization, or mass polymerization.

When the olefin polymerization is carried out in a liquid phase, a solvent acting as a polymerization medium may be a C4-C20 alkane or cycloalkane, such as butane, pentane, hexane, heptane, octane, decan, dodecan, cyclopentane, methylcyclopentane, or cyclohexane; a C6-C20 arene compound, such as benzene, toluene, xylene, or mesitylene; or a C1-C20 haloalkane or haloarene, such as dichloromethane, chloromethane, chloroform, methyltetrachloride, chloroethane, 1,2-dichloroethane, 1,1,2,2-tetrachloroethane, chlorobenzene, 1,2-dichlorobenzene, or 1,2,4-trichlorobenzene. These solvents can be used alone or in combination. However, the solvent is not limited thereto and can be any solvent used in the art.

In the method, the olefin polymerization may be carried out at a pressure of 0.01-1000 atm. When the pressure of the olefin polymerization is less than 0.01 atm, ethylene cannot be effectively supplied and catalyst activation may decrease. On the other hand, when the pressure for the olefin polymerization is more than 1000 atm, the copolymerization of the polar monomer cannot be carried out.

In the method, when the monomer is a monomer mixture that includes ethylene and a comonomer including a polar functional group, the amount of ethylene in the monomer mixture may be in the range of 60-99 mol % and the amount of the comonomer in the monomer mixture may be in the range of 1-40 mol %. When the amount of ethylene in the monomer mixture is less than 60 mol %, catalyst activation may decrease and there can be a problem in a monomer mol ratio of the resultant polymer. On the other hand, when the amount of ethylene in the monomer mixture is more than 99 mol %, it is difficult to synthesize a copolymer.

An olefin-based polymer according to an embodiment of the present invention is prepared using the method.

The olefin-based polymer can be a polar copolymer including 60-99 mol % of ethylene and 1-40 mol % of a polar comonomer.

Substituents of compounds described in the present specification are defined as follows, except when they are specifically defined.

In the present specification, an alkyl group refers to a linear or branched C1-C20 alkyl radical, preferably a linear or branched C1-C12 alkyl radical, more preferably a C1-C6 alkyl radical, and most preferably a C1-C3 alkyl radical. For example, the alkyl group can be methyl, ethyl, n-propyl, isopropyl, n-butyl, isobutyl, sec-butyl, t-butyl, pentyl, isoamyl, or hexyl.

In the present specification, an alkoxy group refers to an oxygen-containing linear or branched radical which includes a C1-C20 alkyl group, preferably a C1-C6 alkoxy radical, and more preferably a C1-C3 alkoxy radical. Examples of the alkoxy group include methoxy, ethoxy, propoxy, butoxy, and t-butoxy. The alkoxy radical can be substituted with at least one halogen atom, such as fluoro, chloro, or bromo to be a haloalkoxy radical, and preferably a C1-C3 low haloalkoxy radical. Examples of the haloalkoxy radical include fluoromethoxy, chloromethoxy, trifluoromethoxy, trifluoroethoxy, fluoroethoxy, and fluoropropoxy.

In the present specification, an alkenyl group refers to a linear or branched C2-C30 aliphatic hydrocarbon group having a carbon-carbon double bond, preferably a linear or branched C2-C12 aliphatic hydrocarbon group having a carbon-carbon double bond, and more preferably a linear or branched C2-C6 aliphatic hydrocarbon group having a carbon-carbon double bond. The branched aliphatic hydrocarbon group may be a linear alkenyl to which at least one low alkyl or low alkenyl group is attached. The alkenyl group may not be substituted or includes halo, carboxy, hydroxy, formyl, sufo, sufino, carbamoyl, amino, and imino. However, the alkenyl group is not limited thererto, and can be independently substituted with at least one functional group. Examples of the alkenyl group include ethernyl, prophenyl, carboxyethernyl, carboxyprophenyl, sulfinoethernyl, sulfonoethernyl etc.

In the present specification, an aryl group can be used alone or in combination. The aryl group refers to a C6-C20 carbocyclic aromatic system including at least one ring. These rings can be attached together using a pendent method or fused. The aryl group may be phenyl, naphthyl, tetrahydronaphthyl, indane, or biphenyl, and preferably phenyl. The aryl group may have one to three substituents selected from hydroxy, halo, haloalkyl, nitro, cyano, alkoxy, and low alkylamino.

In the present specification, an arylalkyl refers to a functional group where an aryl group and an alkyl group are sequentially connected.

In the present specification, an alkylaryl group refers to a functional group where an alkyl group and an aryl group are sequentially connected.

In the present specification, an aryloxy group refers to aryl-O— where the aryl is the same as described above.

In the present specification, a heteroaryl group refers to a monovalent monocyclic or bicyclic aromatic radical having 6-20 ring atoms which consist of one, two, or three hetero atoms selected from N, O, and S and the residual ring atoms are carbons. In addition, the heteroaryl group can refer to a monovalent monocyclic or bicyclic aromatic radical where hetero atoms in the ring are oxidized or quanternized to form, for example, N-oxide or a quaternary salt. Examples of the heteroaryl group include thienyl, benzothienyl, pyridyl, pyrazinyl, pyrimidinyl, pyridazinyl, quinolinyl, quinoxalinyl, imidazolyl, furanyl, benzofuranyl, thiazolyl, isoxazolyl, benzisoxazolyl, benzimidazolyl, triazolyl, pyrazolyl, pyrrolyl, indolyl, 2-pyridonyl, 4-pyridonyl, N-alkyl-2-pyridonyl, pyrazinonyl, pyridazinonyl, pyrimidinonyl, oxazolonyl, N-oxide of these, such as pyridinyl N-oxide and quinolinyl N-oxide, and a quanternized salt of these. However, the heteroaryl group is not limited thereto.

In the present specification, a heteroaryloxy group refers to heteroaryl-O— where the heteroaryl is the same as described above.

In the present specification, a hydrocarbyl group or hydrocarbylene group refers to a functional group that consists of only carbon and hydrogen and can have any structure. For example, the hydrocarbyl group or hydrocarbylene group can be alkyl, aryl, alkenyl, alkylaryl, or arylalkyl.

In the present specification, a heterohydrocarbyl group or heterohydrocarbylene group refers to a hydrocarbyl group including one, two, or three heteroatoms selected from N, O, and S.

The present invention will be described in further detail with reference to the following examples. These examples are for illustrative purposes only and are not intended to limit the scope of the present invention.

Synthesis of Ligand and Metal Compound

Organic reagents and solvents were obtained from Aldrich Co. and Merck Co. and refined using a standard method before use in experiments. The synthesis was carried out excluding air and moisture to increase reproducibility. Structures of compounds were identified based on spectra and charts obtained using a 400 MHz nuclear magnetic resonance (NMR) and an X-ray spectrometer.

EXAMPLE 1

Synthesis of [(HOC$_6$H$_4$-o-C(H)=N—C$_6$H$_4$)$_2$-4-CH$_2$]

2.44 g (20 mmol) of salicylaldehyde dissolved in a methanol solution was added to 1.98 g (10 mmol) of 4,4-methylenedianiline dissolved in a methanol solution. 0.01 g of p-toluenesulfonic acid was added to the resultant solution and then the reaction solution was refluxed for 12 hours. During the refluxing, the reaction solution became gradually transparent and after 12 hours a yellow solid was obtained. The obtained compound was filtered using a filter paper and twice washed using methanol. As a result, 3.8 g of a yellow solid was obtained (Yield: 95%).

$^1$H-NMR (400.13MHz, CDCl$_3$, ppm): δ=13.56 (s, 2H, HO-Ph), 8.63 (s, 2H, H—C=N—), 7.40 (m, 2H, aryl), 7.24 (m, 14H, aryl), 6.79 (m, 2H, aryl), 3.01 (s, 4H, —CH$_2$—)

$^{13}$C-NMR (100.62 MHz, CDCl$_3$, ppm): δ=161.6, 160.1, 145.7, 140.8, 138.3, 131.2, 131.0, 129.5, 122.3, 119.7, 118.7, 39.2.

EXAMPLE 2

Synthesis of [((Ph$_3$P)(phenyl)NiOC$_6$H$_4$-o-C(H)=N—C$_6$H$_4$)$_2$-4-CH$_2$]

A Na salt of 0.61 g (1.5 mmol) of the product obtained according to Example 1 and 2 g (2.88 mmol) of bis(triphenylphosphine)nickel(phenyl)chloride were dissolved in 20 mL of toluene in a reaction container. The resultant solution was mixed for one hour at room temperature and then filtered using a celite-pad to remove a NaCl salt so that the reaction was completely finished. A solvent of the obtained solution was removed under a vacuum condition until the total volume of the obtained solution reached about 5 mL. Then, pentane was added thereto. As a result, a yellow solid was obtained.

$^1$H-NMR (400.13 MHz, C$_6$D$_6$, ppm): δ=7.84 (m, 12H, aryl), 7.65 (m, 2H, aryl), 7.35 (m, 2H, aryl), 7.10 (m, 26H, aryl), 6.80 (t, 2H, aryl), 6.52 (m, 8H, aryl), 6.34 (t, 2H, aryl), 6.25 (t, 4H, aryl), 3.40 (s, 2H, —CH$_2$—).

EXAMPLE 3

Synthesis of [(HOC$_6$H$_4$-o-C(H)=N—C$_6$H$_4$)$_2$-4,4-CH$_2$CH$_2$]

2.44 g (20 mmol) of salicylaldehyde dissolved in a methanol solution was added to 2.12 g (10 mmol) of 4,4-ethylenedianiline dissolved in a methanol solution. 0.01 g of p-toluenesulfonic acid was added to the resultant solution and then the reaction solution was refluxed for 12 hours. During the refluxing, the reaction solution became gradually transparent and after 12 hours a yellow solid was obtained. The obtained compound was filtered using a filter paper and twice washed using methanol. As a result, 3.99 g of a yellow solid was obtained (Yield: 95%).

$^1$H-NMR (400.13 MHz, CDCl$_3$, ppm): δ=13.59 (s, 2H, HO-Ph), 8.65 (s, 2H, H—C=N—), 7.42 (m, 2H, aryl), 7.25 (m, 12H, aryl), 6.87 (m, 2H, aryl), 2.99 (s, 4H, —CH$_2$CH$_2$—);

$^{13}$C-NMR (100.62 MHz, CDCl$_3$, ppm): δ=162.6, 160.5, 146.4, 140.2, 137.6, 130.5, 130.2, 129.5, 121.1, 119.1, 118.3, 37.4.

EXAMPLE 4

Synthesis of [((Ph$_3$P) (phenyl)Ni(OC$_6$H$_4$-o-C(H)=N—C$_6$H$_4$)$_2$-4,4-CH$_2$CH$_2$)]

A Na salt of 0.63 g (1.5 mmol) of the product obtained according to Example 3 and 2 g (2.88 mmol) of bis(triphenylphosphine)nickel(phenyl)chloride were dissolved in 20 mL of toluene in a reaction container. The resultant solution was mixed for one hour at room temperature and then filtered using a celite-pad to remove a NaCl salt so that the reaction was completely finished. A solvent of the obtained solution was removed under a vacuum condition until the total volume of the obtained solution reached about 5 mL. Then, pentane was added thereto. As a result, a yellow solid was obtained.

$^1$H-NMR (400.13 MHz, C$_6$D$_6$, ppm): δ=7.80 (m, 12H, aryl), 7.62 (m, 2H, aryl), 7.31 (m, 2H, aryl), 7.17 (m, 26H, aryl), 6.85 (t, 2H, aryl), 6.60 (m, 8H, aryl), 6.39 (t, 2H, aryl), 6.20 (t, 4H, aryl), 2.88 (s, 4H, —CH$_2$CH$_2$—).

EXAMPLE 5

Synthesis of [(HOC$_6$H$_4$-o-C(H)=N-2,6-(CH$_3$)$_2$C$_6$H$_2$)$_2$-4-CH$_2$]

2.44 g (20 mmol) of salicylaldehyde dissolved in a methanol solution was added to 2.54 g (10 mmol) of 4,4-methylene-bis-2,6-dimethylaniline dissolved in a methanol solution. 0.01 g of p-toluenesulfonic acid was added to the resultant solution and then the reaction solution was refluxed for 12 hours. During the refluxing, the reaction solution became gradually transparent and after 12 hours a yellow solid was obtained. The obtained compound was filtered using a filter paper and twice washed using methanol. As a result, 4.37 g of a yellow solid was obtained (Yield: 95%).

¹H-NMR (400.13 MHz, CDCl₃, ppm): δ=13.58 (s, 2H, HO-Ph), 8.33 (s, 2H, H—C=N—), 7.39 (m, 2H, aryl), 7.18 (m, 4H, aryl), 6.95 (m, 4H, aryl), 6.85 (t, 2H, aryl), 3.84 (s, 2H, (N-2,6-(CH₃)₂Ph)₂-CH₂), 2.20 (s, 12H, N-2,6-(CH₃)₂Ph);
¹³C-NMR (100.62 MHz, CDCl₃, ppm): δ=167.3, 160.7, 146.2, 137.7, 130.4, 130.2, 128.8, 128.6, 118.6, 118.1, 50.8, 40.9, 34.9.

EXAMPLE 6

Synthesis of [((Ph₃P)(phenyl)Ni(OC₆H₄-o-C(H)=N-2,6-(CH3)₂ (4-C₆H₂))₂-4-CH₂)]

A Na salt of 0.69 g (1.5 mmol) of the product obtained according to Example 5 and 2 g (2.88 mmol) of bis(triphenylphosphine)nickel(phenyl)chloride were dissolved in 20 mL of toluene in a reaction container. The resultant solution was mixed for one hour at room temperature and then filtered using a celite-pad to remove a NaCl salt so that the reaction was completely finished. A solvent of the obtained solution was removed under a vacuum condition until the total volume of the obtained solution reached about 5 mL. Then, pentane was added thereto. As a result, a yellow solid was obtained.
¹H-NMR (400.13 MHz, C₆D₆, ppm): δ=7.79 (m, 12H, aryl), 7.59 (m, 2H, aryl), 7.41 (m, 2H, aryl), 7.03 (m, 26H, aryl), 6.81 (t, 2H, aryl), 6.60 (s, 4H, aryl), 6.45 (t, 2H, aryl), 6.19 (t, 4H, aryl), 3.44 (s, 2H, (N-2,6-(CH₃)₂Ph)₂-CH₂), 2.50 (s, 12H N-2,6-(CH₃)₂Ph).

EXAMPLE 7

Synthesis of [(HOC₆H₄-o-C(H)=N-2,6-(CH₃CH₂)₂ (4-C₆H₂))₂-4-CH₂]

2.44 g (20 mmol) of salicylaldehyde dissolved in a methanol solution was added to 3.10 g (10 mmol) of 4,4-methylene-bis-2,6-diethylaniline dissolved in a methanol solution. 0.01 g of p-toluenesulfonic acid was added to the resultant solution and then the reaction solution was refluxed for 12 hours. During the refluxing, the reaction solution became gradually transparent and after 12 hours a yellow solid was obtained. The obtained compound was filtered using a filter paper and twice washed using methanol. As a result, 4.93 g of a yellow solid was obtained (Yield: 95%).
¹H-NMR (400.13 MHz, CDCl₃, ppm): δ=13.59 (s, 2H, HO-Ph), 8.35 (s, 2H, H—C=N—), 7.43 (m, 2H, aryl), 7.20 (m, 4H, aryl), 6.99 (s, 4H, aryl), 6.88 (t, 2H, aryl), 3.95 (s, 2H, (N-2,6-(Et)₂Ph)₂-CH₂), 2.55 (q, 8H, N-2,6-(CH₃CH₂)₂Ph) 1.15 (q, 12H, N-2,6-(CH₃CH₂)₂Ph);
¹³C-NMR (100.62 MHz, CDCl₃, ppm): δ=167.7, 161.2, 146.0, 138.4, 138.2, 135.0, 130.9, 130.7, 127.4, 119.1, 118.6, 41.7, 35.4, 25.3.

EXAMPLE 8

Synthesis of [((Ph₃P)(phenyl)Ni(OC₆H₄-o-C(H)=N-2,6-(CH₃CH₂)₂ (4-C₆H₂))₂-4-CH₂)]

A Na salt of 0.78 g (1.5 mmol) of the product obtained according to Example 7 and 2 g (2.88 mmol) of bis(triphenylphosphine)nickel(phenyl)chloride were dissolved in 20 mL of toluene in a reaction container. The resultant solution was mixed for one hour at room temperature and then filtered using a celite-pad to remove a NaCl salt so that the reaction was completely finished. A solvent of the obtained solution was removed under a vacuum condition until the total volume of the obtained solution reached about 5 mL. Then, pentane was added thereto. As a result, a yellow solid was obtained.
¹H-NMR (400.13 MHz, C₆D₆, ppm): δ=7.83 (m, 12H, aryl), 7.61 (m, 2H, aryl), 7.44 (m, 2H, aryl), 7.11 (m, 26H, aryl), 6.77 (t, 2H, aryl), 6.65 (s, 4H, aryl), 6.48 (t, 2H, aryl), 6.22 (t, 4H, aryl), 3.42 (s, 2H, (N-2,6-(Et)₂Ph)₂-CH₂), 2.50 (q, 8H, N-2,6-(CH₃CH₂)₂Ph), 1.13 (q, 12H, N-2,6-(CH₃CH₂)₂Ph).

EXAMPLE 9

Synthesis of [(HOC₆H₄-o-C(H)=N-2,6-(iso-propyl)₂ (4-C₆H₂))₂-4-CH₂]

2.44 g (20 mmol) of salicylaldehyde dissolved in a methanol solution was added to 3.67 g (10 mmol) of 4,4-methylene-bis-2,6-diisopropylaniline dissolved in a methanol solution. 0.01 g of p-toluenesulfonic acid was added to the resultant solution and then the reaction solution was refluxed for 12 hours. During the refluxing, the reaction solution became gradually transparent and after 12 hours a yellow solid was obtained. The obtained compound was filtered using a filter paper and twice washed using methanol. As a result, 5.46 g of a yellow solid was obtained (Yield: 95%).
¹H-NMR (400.13 MHz, CDCl₃, ppm): δ=13.67 (s, 1H, —OH), 8.31 (s, 2H, H—C=N—), 7.46 (m, 2H, aryl), 7.20 (m, 4H, aryl), 7.06 (s, 4H, aryl), 6.89 (t, 2H, aryl), 4.00 (s, 2H, (N-2,6-(CH(CH₃)₂)Ph)₂-CH₂), 3.11 (sept, 4H, N-2,6-CH(CH₃)₂Ph), 1.16 (d, 24H, N-2,6-CH(CH₃)₂Ph) where Ph represents a phenyl group;
¹³C-NMR (100.62 MHz, CDCl₃, ppm): δ=167.2, 160.5, 146.1, 137.9, 130.2, 130.0, 128.9, 128.5, 118.3, 118.0, 50.6, 40.4, 29.0.

EXAMPLE 10

Synthesis of [((Ph₃P)(phenyl)Ni(OC₆H₄-o-C(H)=N-2,6-(iso-propyl)₂ (4-C₆H₂))₂-4-CH₂)]

A Na salt of 0.86 g (1.5 mmol) of the product obtained according to Example 9 and 2 g (2.88 mmol) of bis(triphenylphosphine)nickel(phenyl)chloride were dissolved in 20 mL of toluene in a reaction container. The resultant solution was mixed for one hour at room temperature and then filtered using a celite-pad to remove a NaCl salt so that the reaction was completely finished. A solvent of the obtained solution was removed under a vacuum condition until the total volume of the obtained solution reached about 5 mL. Then, pentane was added thereto. As a result, a yellow solid was obtained.
¹H-NMR (400.13 MHz, C₆D₆, ppm): δ=7.80 (m, 12H, aryl), 7.63 (m, 2H, aryl), 7.42 (m, 2H, aryl), 7.13 (m, 26H, aryl), 6.80 (t, 2H, aryl), 6.61 (s, 4H, aryl), 6.47 (t, 2H, aryl), 6.21 (t, 4H, aryl), 3.45 (s, 2H, (N-2,6-(iPr)₂Ph)₂-CH₂), 2.55 (sept, 4H, N-2,6-CH(CH₃)₂Ph), 1.12 (d, 24H, N-2,6-CH(CH₃)₂Ph).

EXAMPLE 11

Synthesis of [(HO-(3-tert-butyl)C₆H₃-o-C(H)=N—C₆H₄)₂-4-CH₂]

3.56 g (20 mmol) of 3-t-butylsalicylaldehyde dissolved in a methanol solution was added to 1.98 g (10 mmol) of 4,4-methylene-dianiline dissolved in a methanol solution. 0.01 g of p-toluenesulfonic acid was added to the resultant solution and then the reaction solution was refluxed for 12 hours. During the refluxing, the reaction solution became gradually transparent and after 12 hours a yellow solid was obtained. The obtained compound was filtered using a filter paper and twice washed using methanol. As a result, 4.92 g of a yellow solid was obtained (Yield: 95%).

$^1$H-NMR (400.13 MHz, CDCl$_3$, ppm): δ=13.69 (s, 2H, HO-Ph), 8.65 (s, 2H, H—C=N—), 7.42 (m, 2H, aryl), 7.25 (m, 10H, aryl), 6.87 (m, 2H, aryl), 3.40 (s, 4H, —CH$_2$—) 1.44 (s, 18H, 3-(CH$_3$)$_3$Ph);

$^{13}$C-NMR (100.62 MHz, CDCl$_3$, ppm): δ=162.6, 160.5, 146.4, 140.2, 137.6, 130.5, 130.2, 129.5, 121.1, 119.1, 118.3, 37.4, 34.9, 29.3.

EXAMPLE 12

Synthesis of [((Ph$_3$P)(phenyl)Ni(O—(3-tert-butyl) C$_6$H$_3$-o-C(H)=N—C$_6$H$_4$)$_2$-4-CH$_2$)]

A Na salt of 0.78 g (1.5 mmol) of the product obtained according to Example 11 and 2 g (2.88 mmol) of bis(triphenylphosphine)nickel(phenyl)chloride were dissolved in 20 mL of toluene in a reaction container. The resultant solution was mixed for one hour at room temperature and then filtered using a celite-pad to remove a NaCl salt so that the reaction was completely finished. A solvent of the obtained solution was removed under a vacuum condition until the total volume of the obtained solution reached about 5 mL. Then, pentane was added thereto. As a result, a yellow solid was obtained.

$^1$H-NMR (400.13 MHz, C$_6$D$_6$, ppm): δ=7.83 (m, 12H, aryl), 7.65 (m, 2H, aryl), 7.37 (m, 2H, aryl), 7.12 (m, 28H, aryl), 6.88 (t, 2H, aryl), 6.62 (s, 4H, aryl), 6.40 (t, 2H, aryl), 6.25 (t, 4H, aryl), 3.45 (s, 2H, —CH$_2$—), 1.31 (s, 18H, 3-(CH$_3$)$_3$Ph).

EXAMPLE 13

Synthesis of [(HO—(3-tert-butyl)C$_6$H$_3$-o-C(H)=N—C$_6$H$_4$)$_2$-4,4-CH$_2$CH$_2$]

3.56 g (20 mmol) of 3-t-butylsalicylaldehyde dissolved in a methanol solution was added to 2.12 g (10 mmol) of 4,4-ethylene-dianiline dissolved in a methanol solution. 0.01 g of p-toluenesulfonic acid was added to the resultant solution and then the reaction solution was refluxed for 12 hours. During the refluxing, the reaction solution became gradually transparent and after 12 hours a yellow solid was obtained. The obtained compound was filtered using a filter paper and twice washed using methanol. As a result, 3.99 g of a yellow solid was obtained (Yield: 95%).

$^1$H-NMR (400.13 MHz, CDCl$_3$, ppm): δ=13.61 (s, 2H, HO-Ph), 8.63 (s, 2H, H—C=N—), 7.39 (m, 2H, aryl), 7.21 (m, 10H, aryl), 6.80 (m, 2H, aryl), 2.91 (s, 4H, —CH$_2$CH$_2$—); $^{13}$C-NMR (100.62 MHz, CDCl$_3$, ppm): δ=162.5, 161.0, 145.4, 141.2, 138.6, 130.1, 129.8, 129.0, 120.1, 119.9, 118.5, 37.0.

EXAMPLE 14

Synthesis of [((Ph$_3$P)(phenyl)Ni(O—(3-tert-butyl) C$_6$H$_3$-o-C(H)=N—C$_6$H$_4$)$_2$-4,4-CH$_2$CH$_2$)]

A Na salt of 0.63 g (1.5 mmol) of the product obtained according to Example 13 and 2 g (2.88 mmol) of bis(triphenylphosphine)nickel(phenyl)chloride were dissolved in 20 mL of toluene in a reaction container. The resultant solution was mixed for one hour at room temperature and then filtered using a celite-pad to remove a NaCl salt so that the reaction was completely finished. A solvent of the obtained solution was removed under a vacuum condition until the total volume of the obtained solution reached about 5 mL. Then, pentane was added thereto. As a result, a yellow solid was obtained.

$^1$H-NMR (400.13 MHz, C$_6$D$_6$, ppm): δ=7.80 (m, 12H, aryl), 7.59 (m, 2H, aryl), 7.42 (m, 2H, aryl), 7.15 (m, 28H, aryl), 6.81 (t, 2H, aryl), 6.58 (s, 4H, aryl), 6.43 (t, 2H, aryl), 6.19 (t, 4H, aryl), 2.89 (s, 2H, CH$_2$CH$_2$—), 1.29 (s, 18H, 3-(CH$_3$)$_3$Ph).

EXAMPLE 15

Synthesis of [(HO-(3-tert-butyl)C$_6$H$_3$-o-C(H)=N-2, 6-(methyl)$_2$C$_6$H$_2$)$_2$-4-CH$_2$]

3.56 g (20 mmol) of 3-t-butylsalicylaldehyde dissolved in a methanol solution was added to 2.54 g (10 mmol) of 4,4-methylene-2,6-dimethylaniline dissolved in a methanol solution. 0.01 g of p-toluenesulfonic acid was added to the resultant solution and then the reaction solution was refluxed for 12 hours. During the refluxing, the reaction solution became gradually transparent and after 12 hours a yellow solid was obtained. The obtained compound was filtered using a filter paper and twice washed using methanol. As a result, 5.46 g of a yellow solid was obtained (Yield: 95%).

$^1$H-NMR (400.13 MHz, CDCl$_3$, ppm): δ=13.63 (s, 2H, HO-Ph), 8.34 (s, 2H, H—C=N—), 7.40 (m, 2H, aryl), 7.18 (m, 2H, aryl), 6.95 (s, 4H, aryl), 6.89 (t, 2H, aryl), 3.85 (s, 2H, (N-2,6-(CH$_3$)$_2$Ph)$_2$-CH$_2$), 2.20 (s, 12H, N-2,6-(CH$_3$)$_2$Ph), 1.48 (s, 18H, (CH$_3$)$_3$Ph);

$^{13}$C-NMR (100.62 MHz, CDCl$_3$, ppm): δ=167.5, 160.9, 146.5, 138.0, 137.9, 130.7, 130.5, 129.0, 128.8, 118.9, 118.3, 41.1, 35.2, 29.6, 18.9.

EXAMPLE 16

Synthesis of [((Ph$_3$P)(phenyl)Ni(O—(3-tert-butyl) C$_6$H$_3$-o-C(H)=N-2,6-(methyl)$_2$C$_6$H$_2$)$_2$-4-CH$_2$)]

A Na salt of 0.86 g (1.5 mmol) of the product obtained according to Example 15 and 2 g (2.88 mmol) of bis(triphenylphosphine)nickel(phenyl)chloride were dissolved in 20 mL of toluene in a reaction container. The resultant solution was mixed for one hour at room temperature and then filtered using a celite-pad to remove a NaCl salt so that the reaction was completely finished. A solvent of the obtained solution was removed under a vacuum condition until the total volume of the obtained solution reached about 5 mL. Then, pentane was added thereto. As a result, a yellow solid was obtained.

$^1$H-NMR (400.13 MHz, C$_6$D$_6$, ppm): δ=7.81 (t, 12H, aryl), 7.61 (m, 2H, aryl), 7.40 (m, 2H, aryl), 7.00 (m, 24H, aryl), 6.84 (t, 2H, aryl), 6.55 (s, 4H, aryl), 6.39 (t, 2H, aryl), 6.21 (t, 4H, aryl), 3.53 (s, 2H, (N-2,6-(CH$_3$)$_2$Ph)$_2$-CH$_2$), 2.46 (s, 12H N-2,6-(CH$_3$)$_2$Ph), 0.91 (s, 18H, (CH$_3$)$_3$Ph).

EXAMPLE 17

Synthesis of [(HO-(3-tert-butyl)C$_6$H$_3$-o-C(H)=N-2, 6-(ethyl)$_2$C$_6$H$_2$)$_2$-4-CH$_2$]

3.56 g (20 mmol) of 3-t-butylsalicylaldehyde dissolved in a methanol solution was added to 3.10 g (10 mmol) of 4,4-methylene-2,6-diethylaniline dissolved in a methanol solution. 0.01 g of p-toluenesulfonic acid was added to the resultant solution and then the reaction solution was refluxed for 12 hours. During the refluxing, the reaction solution became gradually transparent and after 12 hours a yellow solid was obtained. The obtained compound was filtered using a filter paper and twice washed using methanol. As a result, 5.99 g of a yellow solid was obtained (Yield: 95%).

$^1$H-NMR (400.13 MHz, CDCl$_3$, ppm): δ=13.68 (s, 2H, HO-Ph), 8.34 (s, 2H, H—C=N—), 7.41 (m, 2H, aryl), 7.18 (m, 2H, aryl), 6.98 (s, 4H, aryl), 6.88 (t, 2H, aryl), 3.94 (s, 2H, (N-2,6-(CH$_3$)$_2$Ph)$_2$-CH$_2$), 2.53 (q, 8H, N-2,6-(CH$_3$CH$_2$)$_2$pH), 1.48 (s, 18H, (CH$_3$)$_3$Ph), 1.15 (t, 12H, N-2,6-(CH$_3$CH$_2$)$_2$Ph);

$^{13}$C-NMR (100.62 MHz, CDCl$_3$, ppm): δ=167.2, 160.7, 145.5, 137.9, 137.7, 134.5, 130.5, 130.3, 127.0, 118.6, 118.1, 41.3, 35.0, 29.4, 24.9, 15.0.

EXAMPLE 18

Synthesis of [((Ph$_3$P)(phenyl)Ni(O—(3-tert-butyl)C$_6$H$_3$-o-C(H)=N-2,6-(ethyl)$_2$C$_6$H$_2$)$_2$-4-CH$_2$)]

A Na salt of 0.95 g (1.5 mmol) of the product obtained according to Example 17 and 2 g (2.88 mmol) of bis(triphenylphosphine)nickel(phenyl)chloride were dissolved in 20 mL of toluene in a reaction container. The resultant solution was mixed for one hour at room temperature and then filtered using a celite-pad to remove a NaCl salt so that the reaction was completely finished. A solvent of the obtained solution was removed under a vacuum condition until the total volume of the obtained solution reached about 5 mL. Then, pentane was added thereto. As a result, a yellow solid was obtained.

$^1$H-NMR (400.13 MHz, C$_6$D$_6$, ppm): δ=7.78 (t, 12H, aryl), 7.58 (m, 2H, aryl), 7.37 (m, 2H, aryl), 6.97 (m, 24H, aryl), 6.80 (t, 2H, aryl), 6.54 (s, 4H, aryl), 6.40 (t, 2H, aryl), 6.20 (t, 4H, aryl), 3.55 (s, 2H, (N-2,6-(Et)$_2$Ph)$_2$-CH$_2$), 2.12 (q, 8H, N-2,6-(CH$_3$CH$_2$)$_2$Ph), 0.91 (s, 18H, (CH$_3$)$_3$Ph), 0.88 (t, 12H, N-2,6-(CH$_3$CH$_2$)$_2$Ph).

EXAMPLE 19

Synthesis of [(HO-(3-tert-butyl)C$_6$H$_3$-o-C(H)=N-2,6-(iso-propyl)$_2$C$_6$H$_2$)$_2$-4-CH$_2$]

3.56 g (20 mmol) of 3-t-butylsalicylaldehyde dissolved in a methanol solution was added to 3.67 g (10 mmol) of 4,4-methylene-2,6-diisopropylaniline dissolved in a methanol solution. 0.01 g of p-toluenesulfonic acid was added to the resultant solution and then the reaction solution was refluxed for 12 hours. During the refluxing, the reaction solution became gradually transparent and after 12 hours a yellow solid was obtained. The obtained compound was filtered using a filter paper and twice washed using methanol. As a result, 6.53 g of a yellow solid was obtained (Yield: 95%).

$^1$H-NMR (400.13 MHz, CDCl$_3$, ppm): δ=13.68 (s, 1H, —OH), 8.30 (s, 2H, H—C=N—), 7.42 (m, 2H, aryl), 7.20 (m, 2H, aryl), 7.03 (s, 4H, aryl), 6.89 (t, 2H, aryl), 4.01 (s, 2H, (N-2,6-(CH(CH$_3$)$_2$)Ph)$_2$-CH$_2$), 3.01 (sept, 4H, N-2,6-CH(CH$_3$)$_2$Ph), 1.49 (s, 18H, (CH$_3$)$_3$Ph), 1.16 (d, 24H, N-2,6-CH(CH$_3$)$_2$Ph);

$^{13}$C-NMR (100.62 MHz, CDCl$_3$, ppm): δ=167.3, 160.7, 144.3, 138.9, 137.8, 130.5, 130.3, 123.8, 118.6, 118.1, 41.6, 35.0, 29.4, 28.1, 23.7.

EXAMPLE 20

Synthesis of [((Ph$_3$P)(phenyl)Ni(O—(3-tert-butyl)C$_6$H$_3$-o-C(H)=N-2,6-(iso-propyl)$_2$C$_6$H$_2$)$_2$-4-CH$_2$)]

A Na salt of 1.03 g (1.5 mmol) of the product obtained according to Example 19 and 2 g (2.88 mmol) of bis(triphenylphosphine)nickel(phenyl)chloride were dissolved in 20 mL of toluene in a reaction container. The resultant solution was mixed for one hour at room temperature and then filtered using a celite-pad to remove a NaCl salt so that the reaction was completely finished. A solvent of the obtained solution was removed under a vacuum condition until the total volume of the obtained solution reached about 5 mL. Then, pentane was added thereto. As a result, a yellow solid was obtained.

$^1$H-NMR (400.13 MHz, C$_6$D$_6$, ppm): δ=7.81 (t, 12H, aryl), 7.61 (m, 2H, aryl), 7.39 (m, 2H, aryl), 7.01 (m, 24H, aryl), 6.82 (t, 2H, aryl), 6.49 (s, 4H, aryl), 6.38 (t, 2H, aryl), 6.23 (t, 4H, aryl), 3.51 (s, 2H, (N-2,6-(iPr)$_2$Ph)$_2$-CH$_2$), 2.12 (q, 8H, N-2,6-(CH$_3$CH$_2$)$_2$Ph), 2.90 (sept, 4H, N-2,6-CH(CH$_3$)$_2$Ph), 0.99 (d, 24H, N-2,6-CH(CH$_3$)$_2$Ph), 0.90 (s, 18H, (CH$_3$)$_3$Ph).

Ethylene Homo Polymerization

EXAMPLE 21

The ethylene homo polymerization was carried out using the transition metal compound obtained according to Example 16 represented by Formula 20.

40 mL of refined toluene and 200 mol of nickelcyclooctadiene (Ni(COD)$_2$) dissolved in a toluene solution acting as a cocatalyst were loaded into a pressure reactor in a high-purity Ar atmosphere. The reactor was left sit in a 30° C. constant temperature bath for 15 minutes so that the reactor and the constant temperature bath had the same temperature. The transition metal compound was prepared in a solution state such that there was a 50 mol toluene per nickel metal. Then, the prepared transition metal compound solution was loaded into the reactor and quickly mixed at 300 r.p.m for 2 hours while ethylene was supplied thereto at 15 bar. Subsequently, an ethanol/hydrochloric acid solution was added to the resultant and mixed for 12 hours and filtered. As a result, a white solid polymer was obtained. Specific experimental conditions and results are shown in Table 1.

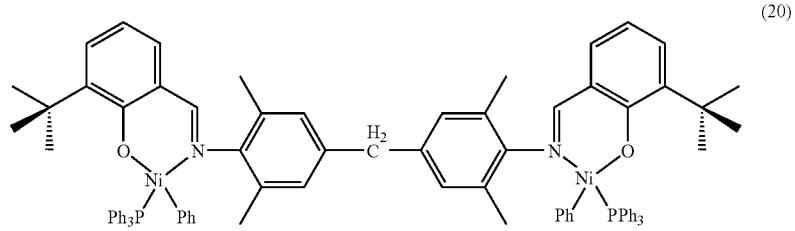

(20)

EXAMPLE 22

Polymerization was carried out in the same manner as in Example 21, except that 9.95 mL of methylaluminoxane (MMAO, 5.65 wt % of Al in toluene solution, density of 0.722) was used as a cocatalyst instead of the 200 mol nickelcyclooctadiene (Ni(COD)₂) dissolved in toluene solution.

EXAMPLE 23

Polymerization was carried out in the same manner as in Example 21, except that the transition metal compound represented by Formula 21 was used instead of the transition metal compound represented by Formula 20.

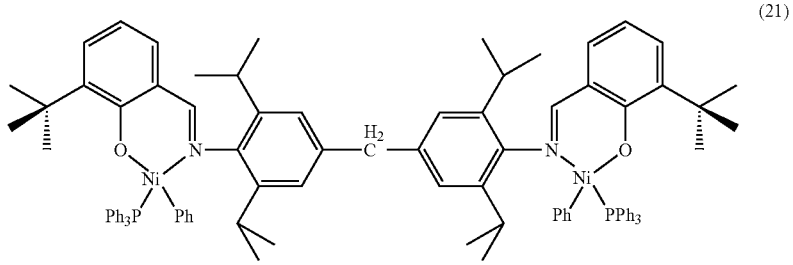

(21)

EXAMPLE 24

Polymerization was carried out in the same manner as in Example 23, except that 9.95 mL of methylaluminoxane (MMAO, 5.65 wt % of Al in toluene solution, density of 0.722) was used as a cocatalyst instead of the 200 mol nickelcyclooctadiene (Ni(COD)₂) dissolved in toluene solution.

COMPARATIVE EXAMPLE 1

Polymerization was carried out in the same manner as in Example 21, except that the transition metal compound represented by Formula 22 (refer to U.S. Pat. No. 6,576,779 B1) was used instead of the transition metal compound represented by Formula 20.

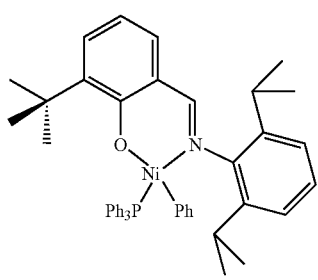

(22)

COMPARATIVE EXAMPLE 2

Polymerization was carried out in the same manner as in Comparative Example 1, except that 9.95 mL of methylaluminoxane (MMAO, 5.65 wt % of Al in toluene solution, density of 0.722) was used as a cocatalyst instead of the 200 mol nickelcyclooctadiene (Ni(COD)₂) dissolved in toluene solution.

TABLE 1

| | Amount of Compound [mol] | Amount of Ni(COD)₂ [mol] | Amount of MMAO (Al/Ni) | Yield (g) |
|---|---|---|---|---|
| Example 21 | 25 | 200 | — | 3.5 |
| Example 22 | 25 | — | 300 | 1.5 |
| Example 23 | 25 | 200 | — | 5.0 |
| Example 24 | 25 | — | 300 | 1.8 |

TABLE 1-continued

| | Amount of Compound [mol] | Amount of Ni(COD)₂ [mol] | Amount of MMAO (Al/Ni) | Yield (g) |
|---|---|---|---|---|
| Comparative Example 1 | 50 | 200 | — | 4.5 |
| Comparative Example 2 | 50 | — | 300 | 1.6 |

* Polymerization Conditions: polymerization temperature (30° C.), polymerization time(2 hours), ethylene pressure(15 bar), toluene(40 mL)

As illustrated in Table 1, during ethylene homo polymerization, yields of polymers obtained according to Examples 21-24 using transition metal compounds according to an embodiment of the present invention were the same or higher than yields of polymers obtained according to Comparative Examples 1 and 2 using conventional transition metal compounds. In particular, when an isopropyl group is contained as a substitutent, catalyst activation was very high, which may be due to a bulky substitutent. In general, catalyst reaction is more promoted in the presence of a bulky substitutent. In addition, in the case of a dinuclear transition metal compound connected by a bridging group, two transition metals are regularly arranged so that the dinuclear transition metal compound is stable with respect to ethylene and provides a very reactive active site.

Copolymerization of Ethylene and Methylacrylate

EXAMPLE 25

Copolymerization was carried out using the transition metal compound used in Example 21.

40 mL of refined toluene and 200 mol of nickelcyclooctadiene (Ni(COD)₂) dissolved in a toluene solution acting as a cocatalyst were loaded into a pressure reactor in a high-purity Ar atmosphere. The reactor was left sit in a 30° C. constant temperature bath for 15 minutes so that the reactor and the constant temperature bath had the same temperature. Then, 7.2 mL (80 mmol) of methylacrylate was added thereto. The dinuclear nickelsalicylaldimine catalyst was prepared in a solution state such that there was a 50 mol toluene per nickel metal. Then, the prepared catalyst solution was loaded into the reactor and quickly mixed at 300 r.p.m for 2 hours while ethylene was supplied thereto at 15 bar. Subsequently, an ethanol/hydrochloric acid solution was added to the resultant solution and mixed for 12 hours and filtered. As a result, a white solid polymer was obtained. Specific experimental conditions and results are shown in Table 1.

EXAMPLE 26

Polymerization was carried out in the same manner as in Example 25, except that 9.95 mL of methylaluminoxane (MMAO, 5.65 wt % of Al in toluene solution, density of 0.722) was used as a cocatalyst instead of the 200 mol nickelcyclooctadiene (Ni(COD)$_2$) dissolved in toluene solution.

EXAMPLE 27

Polymerization was carried out in the same manner as in Example 25, except that the transition metal compound represented by Formula 21 was used instead of the transition metal compound represented by Formula 20.

EXAMPLE 28

Polymerization was carried out in the same manner as in Example 25, except that 9.95 mL of methylaluminoxane (MMAO, 5.65 wt % of Al in toluene solution, density of 0.722) was used as a cocatalyst instead of the 200 mol nickelcyclooctadiene (Ni(COD)$_2$) dissolved in toluene solution.

COMPARATIVE EXAMPLE 3

Polymerization was carried out in the same manner as in Example 25, except that the transition metal compound represented by Formula 22 (refer to U.S. Pat. No. 6,576,779 B1) was used instead of the transition metal compound represented by Formula 20.

COMPARATIVE EXAMPLE 4

Polymerization was carried out in the same manner as in Comparative Example 3, except that 9.95 mL of methylaluminoxane (MMAO, 5.65 wt % of Al in toluene solution, density of 0.722) was used as a cocatalyst instead of the 200 mol nickelcyclooctadiene (Ni(COD)$_2$) dissolved in toluene solution.

TABLE 2

| | Amount of Compound [mol] | Amount of MA [mol/L] | Amount of Ni(COD)$_2$ [mol] | Amount of MMAO (Al/Ni) | Yield (g) |
|---|---|---|---|---|---|
| Example 25 | 25 | 2.0 | 200 | — | 1.0 |
| Example 26 | 25 | 2.0 | — | 300 | 2.2 |
| Example 27 | 25 | 2.0 | 200 | — | 1.6 |
| Example 28 | 25 | 2.0 | — | 300 | 2.6 |
| Comparative Example 3 | 50 | 2.0 | 200 | — | 1.5 |
| Comparative Example 4 | 50 | 2.0 | — | 300 | 2.4 |

*Polymerization conditions: polymerization temperature (30° C.), polymerization time (2 hours), ethylene pressure (15 bar), toluene(40 mL), comonomer (MA, methylacrylate 2.0 mol/L)

As illustrated in Table 2, when copolymerization was carried out using a comonomer including a polar functional group, yields of polymers obtained according to Examples 25-28 using transition metal compounds according to an embodiment of the present invention were the same or higher than yields of polymers obtained according to Comparative Examples 3 and 4 using conventional transition metal compounds. In particular, when an isopropyl group was included in the transition metal compound, catalyst activation was very high. Such high catalyst activation can be obtained by relatively suppressing a decrease in catalyst activation due to a polar functional group, which is known to decrease catalyst activation, as a result of regular interval of two transition metals of a dinuclear transition metal compound connected by a bridging group and the presence of a bulky substituent in the vicinity of an active site.

A transition metal compound according to the present invention includes two transition metal compounds connected by a bridging group so that a decrease in catalyst activation due to a polar functional group can be prevented. A catalyst composition including the transition metal compound is very active with respect to a monomer including a polar functional group.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:
1. A dinuclear transition metal compound represented by Formula 1:

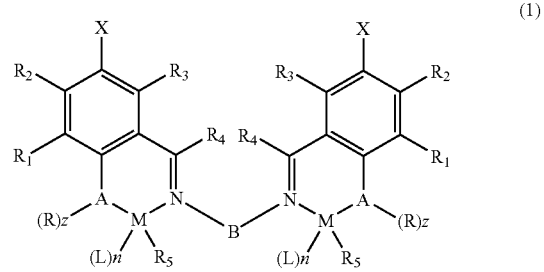

(1)

where R is each independently a hydrogen atom, C1-C11 alkyl, or substituted or unsubstituted aryl, wherein when A is oxygen or sulfur, z is 0, and when A is nitrogen, z is 1;
R$_1$ is each independently a hydrogen atom, C1-C12 alkyl, substituted or unsubstituted arylalkyl or substituted or unsubstituted aryl;
R$_2$ is each independently a hydrogen atom, substituted or unsubstituted aryl, C1-C11 alkyl, or a halogen atom, or can be a substituted or unsubstituted hydrocarbyl which can form an aromatic or nonaromatic carbocyclic ring together with $R_1$;

$R_3$ is a hydrogen atom;

$R_4$ is each independently a hydrogen atom, C1-C11 alkyl, or a substituted or unsubstituted aryl, or can be a substituted or unsubstituted hydrocarbyl which can form a nonaromatic carbocyclic ring together with $R_3$;

n is 1;

when n is 1, $R_5$ is unsubstituted or substituted aryl, C1-C12 alkyl, a hydrogen atom, or a halogen atom;

L is each independently a coordination ligand selected from triphenylphosphine, tri(C1-C6 alkyl)phosphine, tricycloalkyl phosphine, diphenyl alkyl phosphine, dialkylphenylphosphine, triphenoxyphosphine, trialkylamine, C2-20 alkene, halogen, ester, substituted C2-C4 alkene, C1-C4 alkoxy, pyridine, di(C1-C3 alkyl)ether, tetrahydrofurane, and nitrile;

X is each independently an electron acceptor group selected from a hydrogen atom, $NO_2$, halogen, sulfonate ($SO_3^-$), sulfonyl ester ($SO_2R$), carboxyl ($COO^-$), perfluoroalkyl, and carboxylic ester;

M is each independently a Group VI, VII or VIII transition metal selected from Fe, Co, Ni, Ru, Rh, Pd, Os, Ir, and Pt;

A is each independently oxygen, nitrogen, or sulfur; and

B is a covalent bridging group connecting two nitrogen atoms and is carbylene group, a silane group, a disilane group, substituted or unsubstituted C1-C60 hydrocarbylene group, or a substituted or unsubstituted C1-C60 heterohydrocarbylene group including Group 4B, 5B, or 6B atom, wherein, a substituent of the substituted arylalkyl, aryl, allyl, alkene, hydrocarbylene, or heterohydrocarbylene is each independently a C1-C4 alkyl group, a perfluoroalkyl group, a nitro group, a sulfonate group, a halogen group, an arylalkyl group, a siloxyl group ($—OSiE_3$) where E is phenyl or C1-C4 alkyl, or a hydrocarbyl-terminated oxyhydrocarbylene group ($-(GO)_zR_7$) where G is each independently a C1-C4 alkylene group or arylene group, O is oxygen, $R_7$ is a C1-C11 hydrocarbyl group, and z is an integer from 1 to 4.

2. The dinuclear transition metal compound of claim 1, being represented by Formula 2:

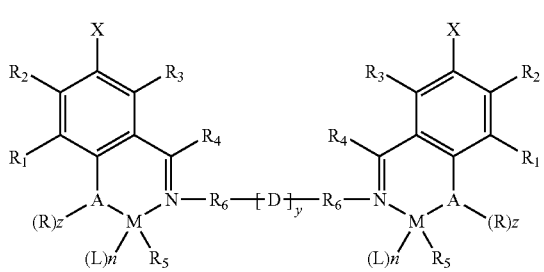

(2)

where $R_6$ is each independently substituted or unsubstituted C1-C12 alkylene, cycloalkylene, arylene, alkylarylene, arylalkylene, or oxyhydrocarbylene ($-(GO)_m$, G-) where G is C1-C4 alkylene or arylene and m is an integer from 1 to 4;

D is saturated or unsaturated alkylene, sulfone, azo, or a carbonyl group, wherein the saturated alkylene includes $—(CR_aR_b)_y—$ where $R_a$ and $R_b$ are each independently a hydrogen atom, C1-C20 alkyl, or C1-C20 aryl, and the unsaturated alkylene includes $—(CH=CH)_y—$ and y is an integer from 0 to 50; and $R_1$, $R_2$, $R_3$, $R_4$, $R_5$, L, R, M, A, X, z, and n are the same as in claim 1.

3. The dinuclear transition metal compound of claim 1, being represented by Formula 3:

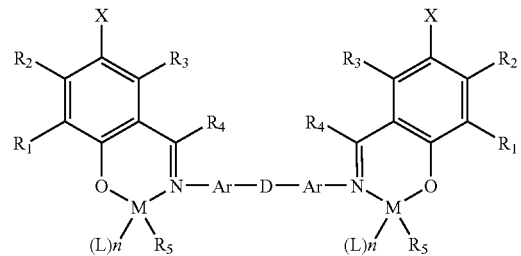

(3)

where Ar is a substituted or unsubstituted arylene group; D is the same as in claim 2: and $R_1$, $R_2$, $R_3$, $R_4$, $R_5$, L, M, and n are the same as in claim 1.

4. The dinuclear transition metal compound of claim 1, being represented by Formula 4:

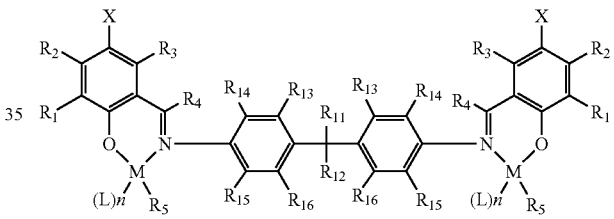

(4)

where $R_{11}$, $R_{12}$, $R_{13}$, $R_{14}$, $R_{15}$, and $R_{16}$ are each independently a hydrogen atom, a halogen, C1-C8 alkyl, or C1-C8 aryl; and $R_1$, $R_2$, $R_3$, $R_4$, $R_5$, L, M, and n are the same as in claim 1.

5. The dinuclear transition metal compound of claim 1, being represented by Formula 5:

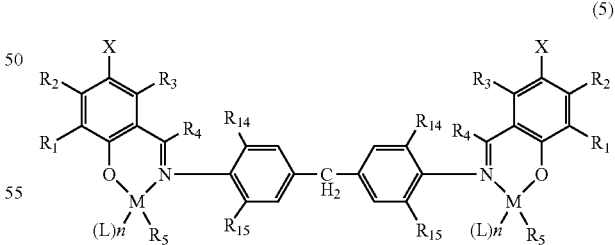

(5)

where $R_{14}$ and $R_{15}$ are each independently C1-C4 alkyl;

M is nickel; and $R_1$, $R_2$, $R_3$, $R_4$, $R_5$, L, and n are the same as in claim 1.

6. A catalyst composition used to polymerize olefin, comprising:

the dinuclear transition metal compound of claim 1; and at least one cocatalyst selected from the group consisting of alkylaluminoxane, alkylaluminium, and Lewis acid.

7. The catalyst composition of claim 6, wherein the alkylaluminoxane is represented by Formula 6:

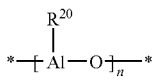  (6)

where $R^{20}$ is a hydrogen atom, a unsubstituted or substituted C1-C20 alkyl group, a unsubstituted or substituted C3-C20 cycloalkyl group, a C6-C40 aryl group, a C6-C40 alkylaryl group, or a C6-C40 arylalkyl group; and n is an integer from 1 to 100.

8. The catalyst composition of claim 6, wherein the alkylaluminium is represented by Formula 7:

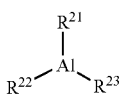  (7)

where $R^{21}$, $R^{22}$, and $R^{23}$ are each independently or at the same time a hydrogen atom, a halogen atom, a unsubstituted or substituted C1-C20 alkyl group, a unsubstituted or substituted C3-C20 cycloalkyl group, a C6-40 aryl group, a C6-40 alkylaryl group, or a C6-40 arylalkyl group, and at least one of $R^{21}$, $R^{22}$, and $R^{23}$ comprises an unsubstituted or substituted C1-C20 alkyl group.

9. The catalyst composition of claim 6, wherein the Lewis acid is represented by Formula 8:

$m(R^{24})_q$  (8)

where M is a Groups 3 through 11 transition metal shown in Periodic Table of Elements;

$R^{24}$ is each independently C1-C20 hydrocarbyl; and q is an integer of 2 through 4.

10. A method of preparing an olefin-based polymer, the method comprising contacting a monomer with the catalyst composition of claim 6.

11. The method of claim 10, wherein the monomer comprises at least one monomer selected from the group consisting of ethylene, a carbonic acid represented by Formula 10, a carbonic acid ester represented by Formula 11 or Formula 12, alkyl vinyl ether represented by Formula 13, vinyl ketone represented by Formula 14, and vinyl alcohol represented by Formula 15:

$CH_2=CH(CH_2)_m COOH$  (10), $CH_2=CH(CH_2)_m CO_2 R^{25}$  (11), $CH_2=CH(CH_2)_m OCOR^{25}$  (12), $CH_2=CH(CH_2)_m OR^{25}$  (13), $CH_2=CH(CH_2)_m C(O)R^{25}$  (14), and $CH_2=CH(CH_2)_m OH$  (15)

where m is an integer from 0 to 10; and $R^{25}$ is C1-C10 hydrocarbyl.

12. The method of claim 10, wherein the olefin polymerization is carried out through slurry polymerization, liquid polymerization, vapor polymerization, or mass polymerization.

13. The method of claim 10, wherein the olefin polymerization is carried out at a pressure of 0.01-1000 atm.

14. The method of claim 10, wherein when the monomer is a monomer mixture of ethylene and a comonomer having a polar functional group, the amount of ethylene is in the range of 60-99 mol % and the amount of the comonomer is in the range of 1-40 mol %, based on the total amount of the monomer mixture.

15. An olefin-based polymer produced using the method of claim 10.

16. The olefin-based polymer of claim 15, wherein the olefin-based polymer is a polar comonomer comprising 60-99 mol % of ethylene and 1-40 mol % of a polar comonomer.

17. A catalyst composition used to polymerize olefin, comprising:
the dinuclear transition metal compound of claim 2; and
at least one cocatalyst selected from the group consisting of alkylaluminoxane, alkylaluminium, and Lewis acid.

18. A catalyst composition used to polymerize olefin, comprising:
the dinuclear transition metal compound of claim 3; and
at least one cocatalyst selected from the group consisting of alkylaluminoxane, alkylaluminium, and Lewis acid.

19. A catalyst composition used to polymerize olefin, comprising:
the dinuclear transition metal compound of claim 4; and
at least one cocatalyst selected from the group consisting of alkylaluminoxane, alkylaluminium, and Lewis acid.

20. A catalyst composition used to polymerize olefin, comprising:
the dinuclear transition metal compound of claim 5; and
at least one cocatalyst selected from the group consisting of alkylaluminoxane, alkylaluminium, and Lewis acid.

21. An olefin-based polymer produced using the method of claim 11.

22. The olefin-based polymer of claim 21, wherein the olefin-based polymer is a polar comonomer comprising 60-99 mol % of ethylene and 1-40 mol % of a polar comonomer.

23. An olefin-based polymer produced using the method of claim 12.

24. The olefin-based polymer of claim 23, wherein the olefin-based polymer is a polar comonomer comprising 60-99 mol % of ethylene and 1-40 mol % of a polar comonomer.

25. An olefin-based polymer produced using the method of claim 13.

26. The olefin-based polymer of claim 25, wherein the olefin-based polymer is a polar comonomer comprising 60-99 mol % of ethylene and 1-40 mol % of a polar comonomer.

27. An olefin-based polymer produced using the method of claim 14.

28. The olefin-based polymer of claim 27, wherein the olefin-based polymer is a polar comonomer comprising 60-99 mol % of ethylene and 1-40 mol % of a polar comonomer.

* * * * *